United States Patent
Roberts

(10) Patent No.: US 7,919,120 B2
(45) Date of Patent: *Apr. 5, 2011

(54) PHARMACEUTICAL SAFETY DOSAGE FORMS

(75) Inventor: Richard H. Roberts, Lakewood, NJ (US)

(73) Assignee: Mutual Pharmaceuticals, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/404,372

(22) Filed: Mar. 16, 2009

(65) Prior Publication Data

US 2009/0175950 A1  Jul. 9, 2009

Related U.S. Application Data

(63) Continuation of application No. 10/339,977, filed on Jan. 10, 2003, now Pat. No. 7,524,515.

(51) Int. Cl.
 *A61K 9/14* (2006.01)
 *A61K 9/16* (2006.01)
 *A61K 9/20* (2006.01)
 *A61K 9/48* (2006.01)

(52) U.S. Cl. ......... 424/489; 424/451; 424/464; 424/490

(58) Field of Classification Search ................. None
See application file for complete search history.

(56) References Cited

U.S. PATENT DOCUMENTS

| | | | |
|---|---|---|---|
| 4,175,119 A * | 11/1979 | Porter | 424/475 |
| 4,371,539 A * | 2/1983 | Stein | 514/364 |
| 4,457,933 A | 7/1984 | Gordon et al. | |
| 4,459,278 A | 7/1984 | Porter | |
| 4,529,583 A | 7/1985 | Porter | |
| 4,769,372 A | 9/1988 | Kreek | |
| 4,885,173 A | 12/1989 | Stanley et al. | |
| 4,981,468 A | 1/1991 | Benefiel et al. | |
| 5,547,878 A | 8/1996 | Kell | |
| 5,795,909 A | 8/1998 | Shasboua et al. | |
| 5,900,423 A | 5/1999 | Ward et al. | |
| 6,004,582 A | 12/1999 | Faour et al. | |
| 6,132,420 A | 10/2000 | Dionne et al. | |
| 6,133,289 A | 10/2000 | Ward et al. | |
| 6,184,248 B1 * | 2/2001 | Lee et al. | 514/474 |
| 6,228,863 B1 | 5/2001 | Palermo et al. | |
| 6,255,502 B1 | 7/2001 | Penkler et al. | |
| 6,337,422 B1 | 1/2002 | Malthe-Sorenssen et al. | |

(Continued)

FOREIGN PATENT DOCUMENTS

EP  1201233 A1  5/2002

(Continued)

OTHER PUBLICATIONS

The PCT International Search Report dated Jul. 2, 2004 (PCT/US03/40990), WO 2004/062642 A1.

(Continued)

*Primary Examiner* — S. Tran
(74) *Attorney, Agent, or Firm* — Cantor Colburn LLP

(57) ABSTRACT

Pharmaceutical safety dosage forms are provided which include a pharmaceutical and an antagonist to the pharmaceutical. The safety dosage forms are such that the antagonist has no significant bioavailability when the pharmaceutical safety dosage form is administered as intended. However, the antagonist is released and becomes bioavailable if the dosage form is disrupted. Methods of administering pharmaceuticals by providing pharmaceutical safety dosage forms are also provided.

11 Claims, 1 Drawing Sheet

U.S. PATENT DOCUMENTS

| | | |
|---|---|---|
| 6,375,957 B1 | 4/2002 | Kaiko et al. |
| 6,440,459 B1 | 8/2002 | Stampa Diez del Corral et al. |
| 6,472,563 B1 | 10/2002 | Tanoury et al. |
| 6,696,088 B2 | 2/2004 | Oshlack et al. |
| 6,716,449 B2 | 4/2004 | Oshlack et al. |
| 7,524,515 B2 * | 4/2009 | Roberts .................. 424/490 |
| 2002/0010127 A1 | 1/2002 | Oshlack et al. |
| 2002/0106329 A1 | 8/2002 | Leslie |
| 2003/0004177 A1 | 1/2003 | Kao et al. |
| 2003/0035839 A1 | 2/2003 | Hirsh et al. |
| 2003/0064099 A1 | 4/2003 | Oshlack et al. |
| 2003/0068276 A1 | 4/2003 | Hughes et al. |
| 2003/0068371 A1 | 4/2003 | Oshlack et al. |
| 2003/0068375 A1 | 4/2003 | Wright et al. |
| 2003/0069263 A1 | 4/2003 | Breder et al. |
| 2003/0125347 A1 | 7/2003 | Anderson et al. |
| 2003/0157168 A1 | 8/2003 | Breder et al. |
| 2003/0220291 A1 | 11/2003 | Renshaw |
| 2004/0006091 A1 | 1/2004 | Kyle et al. |
| 2004/0126323 A1 | 7/2004 | Shevchuk et al. |
| 2004/0126324 A1 | 7/2004 | Hughes |
| 2004/0126428 A1 | 7/2004 | Hughes et al. |
| 2005/0063909 A1 * | 3/2005 | Wright et al. ............. 424/10.1 |
| 2005/0214223 A1 | 9/2005 | Bartholomaeus et al. |

FOREIGN PATENT DOCUMENTS

| | | |
|---|---|---|
| GB | 1428361 | 3/1976 |
| GB | 2162061 A | 1/1986 |

OTHER PUBLICATIONS

Alfonso R. Gennaro, Remington: The Science and Practice of Pharmacy, 19th Edition, 2000, Chapters 45-46.

Howard C. Ansel et al., Pharmaceutical Dosage Forms and Drug Delivery Systems, 7th Edition, 1999, Chapters 6-7, 164-228.

* cited by examiner

PHARMACEUTICAL SAFETY DOSAGE FORMS

CROSS REFERENCE TO RELATED APPLICATION

This application is a continuation of prior application U.S. application Ser. No. 10/339,977 filed Jan. 10, 2003, which is hereby incorporated by reference in its entirety.

FIELD OF THE INVENTION

The present invention relates to the field of pharmaceutical safety dosage forms.

BACKGROUND OF THE INVENTION

Many pharmaceuticals are prone or potentially subject to misuse or abuse when the intended dosing instructions are ignored and/or the written instructions are disregarded. For example, it is well known that sustained-release narcotics, such as OXYCONTIN® ER tablets (supplied by Perdue Pharma), are prone to abuse and misuse when their dosage units are broken, chewed, crushed, dissolved, or otherwise disrupted, rather than being taken whole as intended. Other narcotic and analgesic drugs are liable to similar misuse. Other types of drugs, including those which are not amenable to abuse, may, nonetheless, be inappropriately used. Such inappropriate use can lead to adverse reactions in persons so using the drugs and can give rise to adverse reactions and even death. One example of this is the inappropriate use of metformin sustained-release (e.g., GLUCOPHAGE® XR, metformin hydrochloride extended-release tablets supplied by Bristol-Myers Squibb), a common diabetes drug. If metformin sustained-release is chewed, or the tablets otherwise disrupted prior to ingestion, rather than the tablets being swallowed whole, dangerous lowering of a person's blood glucose level may result. Very large numbers of pharmaceuticals may be inappropriately ingested in this way and a method for reducing or eliminating the undesired effects has long been desired.

Many pharmaceutical products, which have been introduced into the pharmaceutical market in an immediate-release tablet or capsule form, have subsequently been reformulated into a sustained-release form. The sustained-release form has provided the advantages of more convenient dosing schedules, increased patient compliance, more even blood levels, improved therapeutic activity, or others. Typically, the dosage of active pharmaceutical ingredient in these sustained-release formulations is greater than the dosage of the corresponding immediate-release formulation. This presents the danger of "dumping" in which the sustained-release mechanism fails, either intentionally or unintentionally, so that potentially dangerous dosages of the active pharmaceutical ingredient (agonist) are delivered to the patient causing dangerously high blood levels of the agonist. For example, the *Physicians' Desk Reference* (*PDR*), 56th Edition, states for GLUCOTROL®. XL Extended Release Tablets (supplied by Pfizer), under "Information for Patients", that "Patients should be informed that GLUCOTROL XL Extended Release Tablets should be swallowed whole. Patients should not chew, divide, or crush tablets." For the product RITALIN-SR® (supplied by Novartis) under "DOSAGE AND ADMINISTRATION", it is written, "Ritalin-SR tablets must be swallowed whole and never crushed or chewed." For OXYCONTIN® ER tablets (supplied by Perdue Pharma) there has been much recent controversy and numerous published reports of narcotic abuse through mechanical disruption of the sustained-release mechanism thereby enabling the abuser to receive a relatively larger immediate dose of narcotic.

Some attempts at providing dosage forms for preventing abuse of narcotics have been offered by the prior art. For example, U.S. Pat. No. 4,457,933, Gordon et al., discusses both oral and parenteral abuse of strong analgesics, such as oxycodone, propoxyphene and pentazocine. Gordon et al. discuss oral administration of compositions containing specific ratios of oxycodone to naloxone, a narcotic antagonist. According to Gordon et al., the antagonist, naloxone, is supplied in an amount to deter either oral or parenteral abuse of an analgesic without substantially affecting the analgesic activity. Gordon et al., therefore, contemplates that the antagonist be absorbed into the blood in normal use along with the analgesic.

U.S. Pat. No. 5,375,957 in the name of Kaiko et al. recognizes that oral and parenteral abuse of oral opioid formulations can occur by self-administration of more than the prescribed oral dosage. Kaiko et al. discusses an appropriate ratio between analgesic agonist and antagonist in such dosage forms to ensure analgesic efficacy is maintained. Thus, Kaiko et al. contemplates that the antagonist be absorbed into the blood in normal use along with the agonist. Kaiko et al. distinguishes itself over prior art that teaches inclusion of antagonists in oral opioid analgesic dosage forms, which are themselves not orally active, but which counteract the analgesic effects of the opioid upon parenteral administration. As an example, Kaiko et al. describes the commercially available combination of pentazocine and naloxone, wherein the amount of naloxone does not interfere with the pentazocine upon oral administration. As such, it is understood that the antagonist would still be absorbed into the blood in normal use along with the agonist, but would not provide any pharmacological activity.

Pharmaceutical dosage forms that permit absorption into the blood of an antagonist are inefficient because of the resulting potential to hinder the activity of the agonist during normal use. This limits the amount of antagonist that can be used. This also limits the potential amount of antagonist activity that can be incorporated into the dosage form to less than the amount of activity that will substantially inhibit the agonist activity. Even if, as in Gordon et al., the antagonist, naloxone, can be present in amounts that are not orally active, this may not be possible or desirable with antagonists for other drugs. Also, even if the antagonist is not orally active, it may still be absorbed by the blood and impact the patient during normal use of the dosage form. Additionally, as in Gordon et al., if the antagonist is inactive with oral use then it cannot provide protection against dumping of the agonist if the sustained-release tablet is mechanically disrupted. Furthermore, lack of oral activity may not deter oral abuse.

There remains a great need for dosage forms which can minimize or eliminate the effects of abusive or otherwise inappropriate use of pharmaceuticals. A need exists for dosage forms which may be employed for the delivery of a wide range of drugs and which do not require the coadministration of a separate second pharmaceutically active dosage unit in addition to the desired pharmaceutical. Dosage forms which ensure the safe administration of drugs without unnecessarily loading the bloodstream of a person taking the drug with additional dosage units are objects of this invention. A further object is to provide dosage forms which block an avenue of abusive value to a person in possession of the dosage unit. Other objects will become apparent from a review of the present specification.

SUMMARY OF THE INVENTION

Pharmaceutical safety dosage forms are provided by the present invention. Such pharmaceutical safety dosage forms include a pharmaceutical as well as an antagonist for the pharmaceutical. In normal use, that is when the dosage forms are administered or taken by the person in need of drug treatment, the antagonist has no significant bioavailability. The antagonist has significant bioavailability only when the pharmaceutical safety dosage form is disrupted. Disruption of the dosage form means in this context the mechanical, chemical or other alteration of the dosage form in such a fashion as to release or make biologically available the antagonist. Disruption does not mean the dissolution of the dosage form or its delivery of the pharmaceutical in accordance with the intended mechanism of use of the dosage form.

The pharmaceutical safety dosage forms of the present invention can be administered orally, parenterally, rectally, vaginally, transdermally, via aerosol, via nasal spray, or otherwise such as via implantation. In connection with each route of administration, a normal mechanism of delivery of the pharmaceutical is intended consistent with good medical and pharmaceutical practices. Delivery of the pharmaceutical in any of these intended ways for the dosage forms of the invention does not deliver a substantial amount of the antagonist into the bloodstream. Rather, the antagonist is maintained in such a way as not to be substantially bioavailable via such intended method of administration. In short, it is intended that the antagonist "pass through" the patient and be substantially eliminated thereby. Thus, the antagonist is intended not to become bioavailable to the patient and not to require systemic inactivation or excretion therefrom. The overall loading of active compounds is, thus, minimized and limited to only the intended pharmaceutical when the dosage form is used as intended.

The present invention generally contemplates placing one or more antagonist pharmaceutical products within the dosage formulation of the agonist pharmaceutical product so that, under normal conditions, the antagonist is substantially not bioavailable. However, disruption of the formulation, through any of a variety of means, will release the antagonist thereby diminishing the effects of the agonist. For example, for the case of OXYCONTIN® (supplied by Perdue Pharma) Extended Release tablets abuse, narcotic abusers are crushing the tablets to disrupt the sustained-release mechanism thereby gaining a large immediate dose of narcotic. This invention contemplates, in one example, placing a narcotic antagonist in coated beads in OXYCONTIN® (supplied by Perdue Pharma) Extended Release tablets for which the coating maintains the beads intact throughout the digestive system, under normal use, thereby blocking any significant bioavailability of the antagonist. However, when the narcotic abuser crushes the tablets, the abuser will also crush the beads thereby exposing the antagonist within the beads to dissolution in the gastrointestinal tract thereby facilitating bioavailability of the antagonist. There are numerous such examples including, but not limited to, the following: blood glucose lowering drugs such as metformin (e.g., GLUCOPHAGE® XR supplied by Bristol-Myers Squibb) or glipizide (e.g., GLUCOTROL XL® Extended Release Tablets supplied by Pfizer) containing beads of a hyperglycemic agent such as epinepherine or others; anti-hypertensive drugs such as propranolol (e.g., INDERAL® LA Long-Acting capsules supplied by Wyeth-Ayerst), metoprolol (e.g., TOPROL-XL® supplied by AstraZeneca), nifedipine (e.g., PROCARDIA XL® Extended Release tablets supplied by Pfizer, ADALAT® CC supplied by Bayer), diltiazem (e.g., CARDIZEM® CD supplied by Biovail), or nisoldipine (e.g., SULAR® supplied by AstraZeneca) containing beads of antagonist sympathomimetic drugs such as epinepherine or others; methylphenidate (e.g., RITALIN-SR® tablets supplied by Novartis) containing an adrenergic beta blocking drug in beads; any antihistamine with a sympathomimetic decongestant such as cetirizine HCl/pseudoephedrine HCl (e.g., ZYRTEC-D 12 Hour™ Extended Relief tablets supplied by Pfizer), fexofenadine HCl/pseudoephedrine HCl (ALLEGRA-D® Extended-Release tablets supplied by Aventis), or others containing beads containing one or more adrenergic beta receptor blocker drugs; any sustained-release drug could contain an emetic agent within the normally non-bioavailable beads; and numerous other possibilities.

In all of these cases, the effects of the dumping of the active ingredient, whether through intentional abuse, unintentional misuse, or other mechanism could be offset by the resultant release of the antagonist thereby undermining the motivation for abuse or protecting the patient against the harmful effects of dumping of the intended dose.

Figure 1:
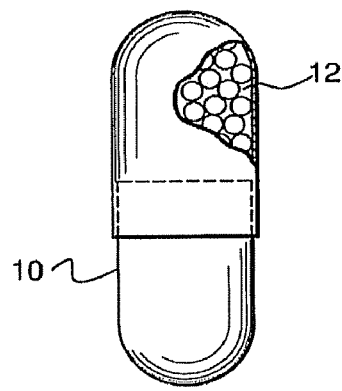
FIG. 1 shows a dosage form of the invention containing pluralities of microdosage forms.

In accordance with the invention, antagonist is delivered from the dosage form, (i.e., becomes bioavailable), only when the dosage form is physically or otherwise disrupted through use in a manner not intended by the drug manufacturer. For example, by reference to only one type of pharmaceutical, with oxycodone sustained-release, for which the present dosage forms are applicable, in normal use, the oxycodone is delivered over a period of time to a patient ingesting a dosage form so as to provide extended narcotic effect to such patient. An antagonist for the narcotic, naloxone, is present in the dosage form, but is not released from the dosage form; it does not become bioavailable, in normal use. However, if the oxycodone dosage form is disrupted, e.g. physically comminuted, in an attempt to release immediately the entire amount of the narcotic in order to abuse the drug, the antagonist, naloxone, is also released. The naloxone is preferably present in an amount sufficient to interfere with the narcotic effect of the oxycodone, thus frustrating the attempted abuse of the drug.

The present dosage forms are amenable to the delivery of a wide variety of narcotic and non-narcotic drugs in a manner having improved safety. The only requirement is a practical one. Thus, a drug which is capable of abuse or of significant adverse effect if inappropriately ingested during or following disruption of the dosage form must be one which has an antagonist. In this context, an antagonist is preferably a compound or composition which is capable of interfering or negating all or some of the effects of the therapeutic drug. This may be achieved either biochemically, physically, physiologically, or otherwise. Thus, while the exemplary narcotic antagonist, naloxone, operates biochemically, it is believed, through interfering with a biochemical (receptor) pathway for narcotics, an effective antagonist, in the context of this invention, may act otherwise, e.g. through stimulation of an excretion or breakdown mechanism for the drug. The mechanism of action of antagonists which may be employed herein is not intended to be limiting in any way. Any compound, group of compounds or composition which can interfere effectively with the action of a drug may be considered to be an antagonist for the drug, providing the overall objectives of this invention are met.

While physical disruption of dosage forms, e.g. comminution or "grinding them up," is an important path undertaken for the abuse or inappropriate use of drugs, non-physical means may also be employed. Thus, dissolution in solvent systems in order to extract drug may be performed. It is preferred that the dosage forms of the present invention release their antagonist component when subjected to such solvent action if the particular intended activity of the antagonist is to counteract the effects of this solvent disruption. Conceivably, a dosage form could be melted or sublimed to release a drug. In such cases, it may be preferred that dosage forms be available which can release antagonist under such conditions if this is the particular activity that is intended to be counteracted by inclusion of the antagonist in the dosage form. The antagonist can be formulated to protect against one or more such disruption activities.

Many pharmaceuticals are provided in capsule dosage forms containing within them microdosage forms. One embodiment of the present invention provides a pharmaceutical and an antagonist for the pharmaceutical in a dosage form where each is contained within microdosage forms, e.g., coated beads, mini tablets, and tablets. Thus, for example, the beads containing the drug are coated or formulated so as to release the drug on an intended time profile. The beads containing the antagonist, however, are either formulated or coated so as to prevent significant bioavailability of the antagonist when the dosage form is consumed as intended. Specific coatings which can attain the foregoing objectives are numerous and well-known to pharmaceutical chemists and formulators. Their identity and use in achieving coatings or formulations in accordance with the present requirements are not a central part of this invention and it is to be understood that all such coatings and formulations are comprehended hereby. It is understood, for example, that it may be desirable in some formulations to use only a single coating, whereas it may be desirable in other formulations to use multiple coatings, and the embodiments of the present invention are not intended to be limited thereby.

An exemplary, but by no means exhaustive, compilation of coatings and formulations for solid dosage forms, and the like is contained within *Remington: The Science and Practice of Pharmacy* by Alfonso R. Gennar, editor, (19th edition 2000) (Chapters 45-46) and *Pharmaceutical Dosage Forms and Drug Delivery Systems* by Howard C. Ansel, et al. (Chapters 6-7), each incorporated herein by reference to provide guidance on such technologies.

Figure 1A:
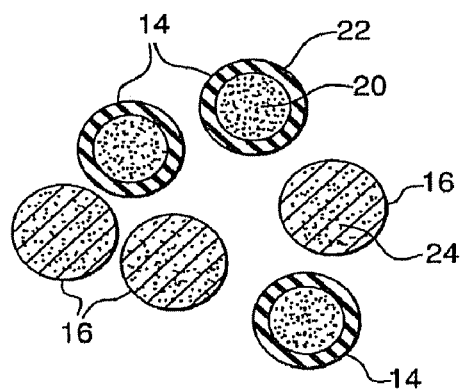
FIG. 1A depicts two different types of bead types of microdosage forms.

An exemplary dosage form employing beads in accordance with the foregoing discussion is presented in FIG. 1. FIG. 1 depicts a conventional capsule dosage form comprising a shell, 10 and containing pluralities of microdosage forms, e.g. beads, 12. There are preferably at least two different kinds of beads, beads (or other microdosage forms) containing the drug and beads (or other microdosage forms) containing antagonist. The drug-containing beads are formulated so as to release drug when administered to a patient in accordance with conventional practice. The antagonist-containing beads are formulated so as not to deliver antagonist to a patient in normal use. Thus, for example, as shown in FIG. 1A, beads 16 can represent a formulated drug 24 within a saccharide, polymer, or other matrix designed to deliver the drug, e.g. in the small intestine of a patient. Another type of bead 14 comprises antagonist for the drug 20 coated by coating 22 the whole being formulated to resist antagonist delivery until all beads are eliminated from the patient, e.g. in the stool. As discussed, however, the drug-containing beads may be coated and the antagonist not coated as may be desired by the routineer in the art. Moreover, three or more different types of beads may be employed, for example, when extended-release of drug is desired or there are different active ingredients. As stated, the preparation of diverse types of beads and the use of a wide variety of coatings and formulation components is an advanced art and is well known to persons skilled in drug formulation. All such may find utility herein.

Figure 1B:
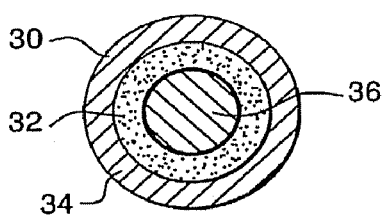
FIG. 1B shows a multi-layered bead for use in one embodiment of the invention.

A further exemplification of the invention is shown in FIG. 1B. The figure depicts a multi-layer microdosage form or bead 30. Drug 32 is coated by coating 34 designed to deliver the drug to a patient at a desired time and in a desired location, e.g. the stomach. The whole, in this embodiment, preferably surrounds a formulation of antagonist 36 for the drug which is so formulated as not to release antagonist when ingested under normal conditions. Thus, the antagonist is designed to pass through the body of the patient unabsorbed.

If any of these exemplary embodiments are subjected to physical disruption, e.g. by being ground up, both the drug and the antagonist are likely to be released. The dosage forms are, thus, less amenable to abuse if crushed or chewed by a patient. Furthermore, such dosage forms provide protection against unexpected dosing upon crushing or chewing because the patient will receive both the unexpected dosing and the antagonist which will diminish the effect of the unexpected dosage. Increased resistance to abuse and overdose result.

Figure 4:
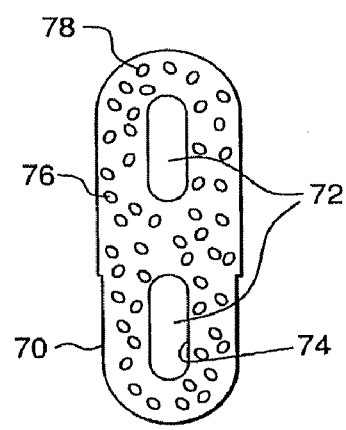
FIG. 4 shows a dosage form of the invention containing two different types of microdosage forms.

Another exemplary dosage form using different types of microdosage forms is shown in FIG. 4. FIG. 4 presents a conventional capsule dosage form comprising a shell 70, and containing two different types of microdosage forms, e.g., tablets 74 and beads 78. It is understood that neither the drug nor its antagonist are limited to certain microdosage forms. Thus, in one instance, a drug 72 may be contained in tablets 74 which are formulated for time-release, and its antagonist 76 may be contained in beads 78 formulated or coated to not deliver the antagonist during normal use of the dosage form. On the other hand, it is possible that the drug may be contained in beads formulated for time-release and its antagonist may be contained in tablets coated to prevent significant bioavailability when the dosage form is used as intended.

Many pharmaceuticals are also provided in tableted or capsule dosage forms comprising some particulated forms of ingredients. A further embodiment of the present invention comprises a drug in the form of a powder, in an amorphous form or with one or more polymorphs, in tabletable form together with antagonist in a microdosage form such that it is substantially insoluble in gastric or other fluid. Thus, for example, a powdered drug, along with excipients, such as fillers, binders, disintegration agents, lubricants, colorants, or other conventional adjuvants, is combined with one or more beads, mini tablets, powder, or other forms containing antagonist. The antagonist forms are formulated or coated in such a way as to render them substantially insoluble in the gastrointestinal tract or other locus of administration. An antagonist that is substantially insoluble in the human body, for example, is prevented from being released before the antagonist is excreted from the body. It is understood in the art that powders can be formulated so as to prevent dissolution in bodily fluids and/or prevent significant bioavailability. Solubility of polymorphs or solvates, for example, are dependent on the crystallized structure of the molecules, and thus, have different solubilities. Hence, certain polymorphs or solvates may be insoluble in the body, but readily soluble in specific solvents. The preparation of polymorphs or solvates are discussed by numerous patents on numerous molecules, e.g. U.S. Pat. Nos. 6,472,563; 6,440,459; 6,337,422; 6,133,289; and 5,900,423. Also contemplated is using one or more polymorphic or solvate forms of one or more antagonists wherein the utilized polymorphic or solvate forms are not readily bioavailable under normal use.

Figure 3:
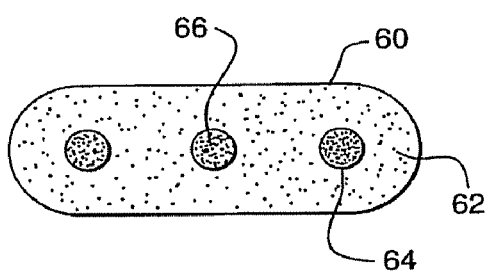
FIG. 3 shows a dosage form of the invention containing microdosage forms and particulated forms.

In FIG. 3, a tableted dosage form in accordance with one embodiment of the invention is provided. The tableted dosage form 60 is formed from powdered drug 62 together with conventional adjuvants, such as excipients and the like. Beads, mini tablets, or the like 64 comprising antagonist for the drug 66 are included within the tablet. Other variations of such tableted dosage forms may also be employed. It is understood that neither the drug nor its antagonist are limited to certain particulated forms or microdosage forms. Thus, a drug may be present in time-release powder form and its antagonist may be present as a polymorph which is insoluble in the body, but readily soluble in specific solvents. Furthermore, pharmaceutical safety dosage forms themselves are not limited in the types of microdosage forms or particulated forms contained therein. As such, a conventional capsule dosage form, for example, may contain a drug in time-release powdered form and an antagonist to the drug in tableted form, shellacked to prevent bioavailability upon normal use of the dosage form.

Figure 2:
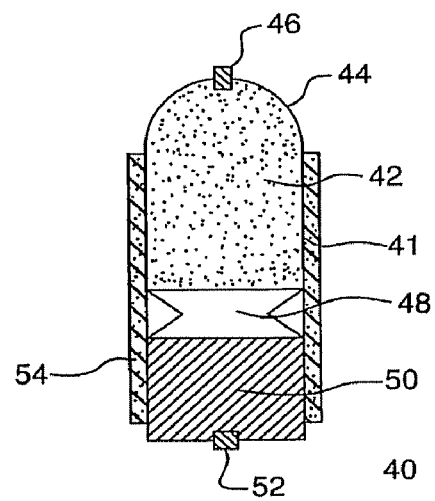
FIG. 2 depicts an osmotic drug dosage form in accordance with the invention.

A further dosage form in accordance with this invention is depicted in FIG. 2. This is a type of osmotic pump drug delivery dosage form 40. Thus, a shell 41 contains a compartment containing drug 42 as well as a compartment containing an osmotic agent 50. The two compartments are preferably separated by a piston 48. Preferably, both the drug-containing compartment and the osmotic agent-containing compartment have an orifice sealed by plugs 46 and 52, respectively. Upon administration, such as oral administration, the plugs 46 and 52 dissolve, exposing both the drug-containing compartment and the osmotic agent-containing compartment to body fluid. Absorption of water by the osmotic agent with concomitant swelling pushes upon the piston 48, expelling the drug through the orifice to its compartment. The geometry of the dosage form, orifice sizes, identity of the drug and osmotic agent and other factors are typically designed and optimized for a desired delivery location and timing. The art of osmotic drug delivery is relatively mature and an extensive patent literature has arisen. Moreover, commercial sources for such dosage forms are available, e.g. the Alza Corporation. One exemplary patent showing such dosage forms is U.S. Pat. No. 6,132,420.

The present invention may be applied to such osmotic drug dosage forms. In one embodiment, shown in FIG. 2, a formulation of antagonist, 54 surrounds the dosage form. In view of the importance of the orifices to operation of the dosage form, the antagonist formulation is generally kept away from those orifices as shown. Since osmotic drug delivery vehicles may take a diversity of physical shapes, the shape and location of antagonist will reflect such geometry. While, as shown, the antagonist formulation is one which does not release antagonist to the body of a person correctly ingesting the dosage form, it may also be coated if preferred to achieve a similar result. In any event, physical or other disruption of the dosage form will release the antagonist as well as the drug. Another example could be coated beads of the antagonist that reside in one or more compartments of the osmotic drug delivery vehicle.

Another aspect of the present invention is a method of administering pharmaceuticals by providing pharmaceutical safety dosage forms that include a pharmaceutical and an antagonist for the pharmaceutical where the microdosage forms provide insignificant bioavailability when the dosage form is administered as intended.

Insignificant bioavailability in the context of this invention is intended to mean that the antagonist does not interfere with the drug in a meaningful way and that the person to whom the dosage form is administered is not burdened with a significant loading of antagonist.

Drug dosage forms of this invention are preferably administered through the alimentary canal orally or anally. Delivery otherwise to the body from outside of the digestive tract, parenteral administration, may also benefit from this invention and employs, e.g. subcutaneous, intravenous, intravaginal, intramuscular, transdermal, nasal, aerosol, or other routes of administration.

The use of the present pharmaceutical safety dosage forms is directly applicable to administration of drugs prone to drug abuse, such as narcotics and amphetamines. One combination of agonist and antagonist contemplated by the present invention includes narcotics and narcotic antagonists. Examples of narcotics include, but are not limited to, codeine, oxycodone, propoxyphene, pentazocine, and derivatives thereof. Examples of narcotic antagonists include, but are not limited to, naloxone, nalmefene, and derivatives thereof. Another combination of agonist and antagonist is sympathomimetics, e.g. amphetamines, and adrenergic beta blockers. Sympathomimetic agonists along with antihistamines can also be combined with adrenergic beta blockers. Reference to derivatives of chemicals discussed herein include, but are not limited to, chemical derivatives and salts and bases thereof.

Drugs which are not prone to abuse may also be administered using the safety dosage forms hereof. Thus, drugs intended for sustained-release in the body can give rise to unpleasant and undesired reactions if over-administered. Thus, the disruption of dosage forms containing, e.g. diabetes drugs, blood pressure lowering drugs and many other types of pharmaceuticals can give rise to diabetic shock or shock-inducing low blood pressure. Such conditions can be fatal. Examples of diabetes drugs include, but are not limited to, hypoglycemic agents, and examples of antagonists to hypoglycemic agents include, but are not limited to, hyperglycemic agents. Examples of blood pressure-lowering drugs include, but are not limited to, adrenergic beta blockers, calcium channel blockers, and ACE inhibitors. Examples of antagonists to blood pressure-lowering drugs include, but are not limited to, sympathomimetics. Including antagonists for these drugs as taught hereby can guard against accidental overdose, if, for example, sustained-release tablets are chewed.

Furthermore, in accordance with the present invention, dosage forms can include any pharmaceutical combined with an emetic agent, e.g., ipecac, which is released upon disruption of the dosage forms.

While not intended to be limiting, an exemplary list of drugs (as bases or any salts thereof) and their antagonists are set forth which may find utility through delivery via the safety dosage forms of this invention.

| DRUG | ANTAGONIST |
| --- | --- |
| Codeine, Oxycodone, Propoxyphene, Pentazocine, Buprenorphine, Morphine, Oxymorphone | Naloxone, Nalmefene, Naltrexone |
| Methamphetamine, amphetamine, dextroamphetamine, methylphenidate | Propranolol, Atenolol, Metoprolol, or other andrenergic beta blocker |
| Insulin, Metformin, Glipizide | Epinepherine, Glucagon |
| Propranolol, Metoprolol, Nifedipine, Diltiazem, Nisoldipine, Timolol Maleate | Dopamine, Epinepherine or other sympathomimetic |
| Methylphenidate | Adrenergic beta blocker |
| Cetirizine HCl/pseudoephedrine HCl, fexofenadine HCl/pseudoephedrine HCl | Adrenergic beta blocker |
| Any drug | Ipecac or other emetic agent |

Other aspects of the invention will be apparent from review of the present specification and claims and all such falling within the spirit of the invention are comprehended hereby.

What is claimed is:

1. A pharmaceutical safety dosage form comprising an amphetamine and an antagonist for the amphetamine;
   wherein the antagonist is an adrenergic beta blocker that is propranolol, atenolol, metoprolol, derivatives thereof, or combinations thereof;
   wherein the amphetamine is contained within a first microdosage form being adapted for release of the amphetamine within a patient, together with the adrenergic beta blocker, wherein the adrenergic beta blocker is contained within a second microdosage form, the second microdosage form being substantially insoluble in gastric fluid;
   wherein the first form is time-release, or the second form comprises an insoluble coating, or both; and
   wherein the antagonist has significant bioavailability only when the pharmaceutical safety dosage form is disrupted.

2. The pharmaceutical safety dosage form of claim 1, wherein the amphetamine is methamphetamine, amphetamine, dextroamphetamine, derivatives thereof, or combinations thereof.

3. The pharmaceutical safety dosage form of claim 1, further comprising an antihistamine.

4. The pharmaceutical safety dosage form of claim 3, wherein the antihistamine is cetirizine HCl, fexofenadine HCl, derivatives thereof, or combinations thereof.

5. The pharmaceutical safety dosage of claim 1 wherein the amphetamine is adapted for time-release, or the antagonist comprises an insoluble coating, or both.

6. The pharmaceutical safety dosage form of claim 1 wherein the bioavailability occurs upon mechanical disruption or upon extraction by a chemical.

7. The pharmaceutical safety dosage form of claim 1 adapted to be administered orally.

8. The pharmaceutical safety dosage form of claim 1, wherein the first microdosage form comprises particles, beads, tablets, mini tablets, or combinations thereof; or the second microdosage forms comprises particles, beads, tablets, mini tablets, or combinations thereof; or both.

9. The pharmaceutical safety dosage form of claim 1, wherein the amphetamine is in a first form adjacent to the adrenergic beta blocker in a second form.

10. The pharmaceutical safety dosage form of claim 9, wherein the first form is substantially layered over the second form.

11. The pharmaceutical safety dosage form of claim 9, wherein the second form is substantially layered over the first form.

* * * * *